United States Patent [19]
Chaffringeon

[11] Patent Number: 5,810,745
[45] Date of Patent: Sep. 22, 1998

[54] SINGLE-USE BODY FLUID ANALYSIS DEVICE

[76] Inventor: Bernard Chaffringeon, 10 avenue du Léman, 1025 Saint-Sulpice, Switzerland

[21] Appl. No.: 793,947
[22] PCT Filed: Sep. 19, 1995
[86] PCT No.: PCT/FR95/01199
§ 371 Date: Mar. 4, 1997
§ 102(e) Date: Mar. 4, 1997
[87] PCT Pub. No.: WO96/09544
PCT Pub. Date: Mar. 28, 1996

[30] Foreign Application Priority Data

Sep. 19, 1994 [FR] France .................................. 94 11349

[51] Int. Cl.$^6$ ....................................................... A61B 5/00
[52] U.S. Cl. ............................................................. 600/581
[58] Field of Search ..................... 600/573, 581, 600/584; 604/317

[56] References Cited

U.S. PATENT DOCUMENTS 3,850,160  11/1974  Denson .
4,227,537  10/1980  Suciu et al. .
4,257,427   3/1981  Bucalo .
4,614,715   9/1986  Tsibris et al. .

FOREIGN PATENT DOCUMENTS

| 0 166 933 | 8/1986 | European Pat. Off. . |
| 0 228 752 | 7/1987 | European Pat. Off. . |
| 0 363 196 | 11/1990 | European Pat. Off. . |
| 0 555 109 A2 | 11/1993 | European Pat. Off. . |
| 0 555 109 A3 | 11/1993 | European Pat. Off. . |
| WO 91/09309 | 6/1991 | WIPO . |

*Primary Examiner*—Max Hindenberg
*Attorney, Agent, or Firm*—Oliff & Berridge, PLC

[57] ABSTRACT

A single use device for analyzing a body fluid in an elongate body cavity including a pipe element with a neck and a bottom wall and a liquid transfer assembly partially located within the element and extending through a sampling region outside the neck to an axial collection point located within said element in the region of the bottom wall.

20 Claims, 2 Drawing Sheets

SINGLE-USE BODY FLUID ANALYSIS DEVICE

BACKGROUND OF THE INVENTION

The present invention relates to the analysis of a body fluid taken directly from an elongate intra-corporeal cavity. By way of a nonlimiting example, the present invention will be introduced, defined and explained with reference to the recovery of the cervical mucus in the vaginal cavity of women for detection of the period of fertility.

In order to determine the periods of fertility in women, it is known, and it has been proposed, to detect and monitor the presence and/or concentration of certain biochemical or biological constituents of said mucus, such as a peroxidase or a compound having a peroxidase activity, or such as a mucopolysaccharide or a glycoprotein, by using reagents or colored reagent systems, for example, in the former case, an oxidation-reduction compound, of which at least the oxidized form is colored, for example guaiacol, and in the latter case safranin.

The solutions which have been proposed for the use of such reagents or reactive systems have generally been rudimentary and have in practice been difficult for women to put into use, namely:

taking a sample of the cervical mucus in situ, with an element capable of recovering the mucus, such as a swab, then bringing said element into contact, outside the vaginal cavity, with the reagent in liquid form;

introducing into the vaginal cavity an absorbent tampon impregnated or coated with a layer of reagent, and withdrawing said tampon after a certain time, and treating the layer of reagent with a color-developing agent.

These methods are known, for example, from the documents FR-A-2,216,975, EP-A-0,363,196 and EP-A-0,555,109.

The disadvantages of these methods result from the need to treat the extract of cervical mucus recovered extemporaneously, in order to reveal the possible presence or concentration of certain of its biochemical constituents.

Furthermore, in order to culture microorganisms directly, in particular pathogens, which may be present in an elongate intracorporeal cavity, a disposable device according to the embodiment in FIG. 3 of the document US-C-4,257,427 has been proposed, said device comprising:

a conduit element, made of transparent plastic, surrounded by a sheath of flexible foam; this element has, at its two ends, a relatively narrow neck and a base; it is inherently sufficiently stiff or rigid along its length for it to be pushed via its base and introduced into the intracorporeal cavity;

a means for transferring the body fluid assumed to contain the microorganisms, said means being mounted at least in part in the interior of the conduit element, extending from a zone for sampling of the body fluid, outside the neck, to an axial collection point for said fluid, situated inside the conduit element, toward its base; this means consists of a wick of braided filaments, the outer unravelled end of which serves for taking the samples, and the inner end of which concentrates the body fluid which has been collected; an intermediate tube ensures sealing between the wick and the neck of the conduit element in such a way that the interior of the latter is substantially isolated from the intracorporeal cavity in which said element has been introduced;

a culture medium arranged inside the conduit element, against its base.

This device is introduced by the user into the intracorporeal cavity, in which it remains for a period of time sufficient to permit the recovery of the body fluid, and the culturing of the microorganisms sought. The user then removes the device from the intracorporeal cavity and observes the development, or lack of development, of the culture of the microorganism sought, through the wall of the conduit element.

SUMMARY OF THE INVENTION

The subject of the present invention is a disposable device permitting extemporaneous analysis of a body fluid, with results which can be identified directly by the user, and without any intervention by the latter, other than that of introducing and removing said device into and from the intracorporeal cavity.

In accordance with the present invention, the starting point is a disposable device such as is described in the document US-C-4,257,427, which device is then modified specifically in the following manner:

on the one hand, the sampling zone of the transfer means consists of a peripheral ring, supported in the aperture of the neck of the conduit element, protruding radially and to the outside of said neck, and forming a passage for communication between the intracorporeal cavity and the inside of said conduit element;

and, on the other hand, a reaction means is mounted or arranged on the conduit element, in a manner visible to the user, and in relation with the axial collection point, in order to receive at least some of the body fluid which has been collected, and it comprises at least one reagent capable of reacting with at least one component of the body fluid, or in the presence of a biological or biochemical state of said fluid, in order to give a reaction product, preferably colored, revealing the presence of said biological or biochemical state, or of said component in said body fluid, and directly identifiable by the user.

By virtue of the present invention, the recovery in particular of the body fluid remains independent of the differential pressure conditions between the intracorporeal cavity and the inside of the conduit element, this fact facilitating the transfer of the body fluid toward the reaction means. This advantage is decisive when the body fluid, for example the cervical mucus, is more or less liquid, and/or more or less abundant.

The conduit element 2 is preferably adapted in shape and dimensions to be fitted and held directly, by simple constriction [sic], in the intracorporeal cavity, and its outer surface is chosen to be biocompatible with the inner wall of the intracorporeal cavity.

The term "biocompatible" refers to the fact that the contact between the outer surface of the conduit element and the wall of the intracorporeal cavity does not generate any adverse biological reaction, for example of the toxic or allergic type.

The means for transferring the body fluid advantageously comprises a bundle of filiform elements which are gathered together at one end at the axial collection point and are spread out at the other end about the peripheral sampling ring, each filiform element being capable of conveying the body fluid from an outer end to an inner end, for example by absorption or capillarity.

The filiform elements are preferably hollow filaments, or else comprise fibers of at least one biocompatible polymer, in particular a polymer chosen from among the hydrophilic natural or synthetic polymers, such as polyesters, polyacrylonitriles, polycarbonates, polyethylenes and polypropylenes, silicones, alginates, polyurethane foams, or else cellulose or its esters, optionally impregnated with an agent liquefying the body fluid.

The reaction means is preferably arranged inside the conduit element, at its closed base, facing the axial collection point of the transfer means.

In this case, the base of the conduit element is transparent, and the reagent is arranged against this base, and in fact faces the axial collection point of the transfer means, in such a way that when the reaction product is colored, this color or absence of color can be seen or visualized by the user.

In a variant according to the invention, the base is at least partially open, and a stem for transfer of the body fluid, from the axial collection point to a distal element for recovery of said fluid, passes through the base via its aperture and emerges from the conduit element.

In this case, the transfer stem preferably consists of the same filiform elements as for the transfer means, which may optionally continue through the base of the conduit element, and the reaction means can be the same or different, depending on whether the aim is to demonstrate a biological component or biological state, or two different biological components or states.

This variant has the advantage of indicating the presence or absence of a biological state or component of the body fluid without the user being obliged to withdraw the device from the intracorporeal cavity.

The analysis device according to the invention, as it has been described, can therefore be used directly, in particular without subsequent addition of color reagent or developer by the user, and in this latter case the color reaction is observed immediately after the removal of the device.

BRIEF DESCRIPTION OF THE DRAWINGS

The present invention is now described with reference to the attached drawing, in which.

DETAILED DESCRIPTION OF PREFERRED EMBODIMENTS

Figure 1:
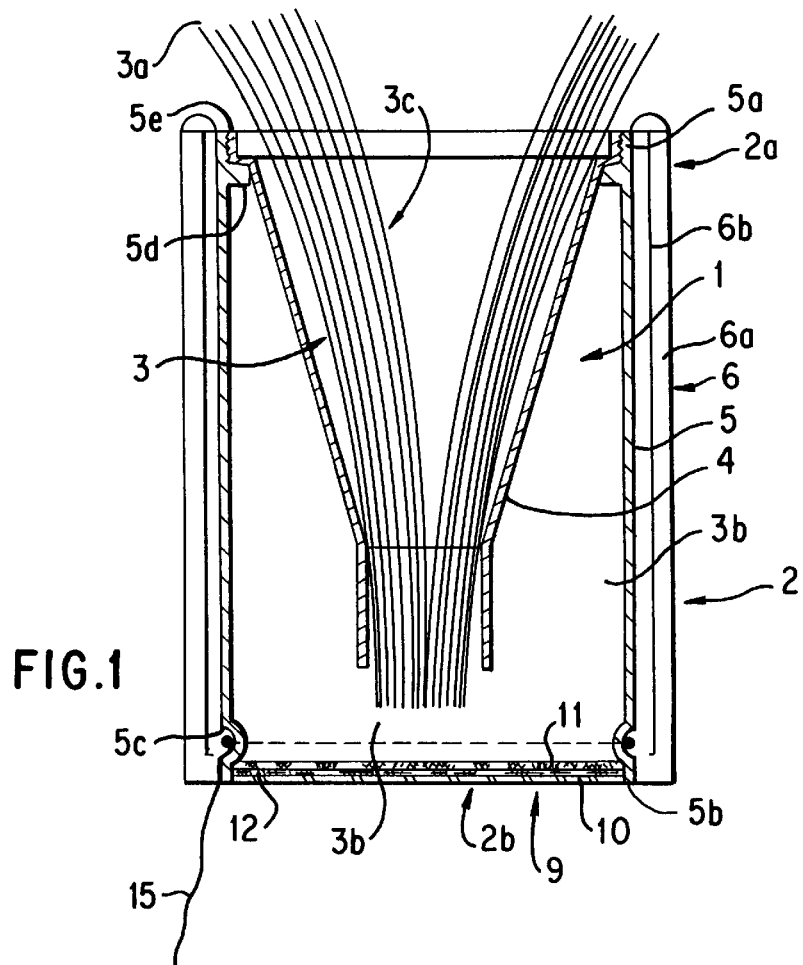
FIG. 1 represents a cross section of a disposable analysis device according to the invention.

In a general manner, and as illustrated in FIG. 1, a disposable analysis device 1 for recovery of body fluid, for example cervical mucus, directly from an elongate intracorporeal cavity, for example the vaginal cavity, comprises:

a conduit element 2 adapted in shape and dimensions to be fitted directly in, and held by simple constriction of, the intracorporeal cavity; this element has at its two ends, respectively, a relatively wide neck 2a and a base 2b having the same cross section; this element is inherently sufficiently stiff or rigid along its length to be pushed via its base 2b, and introduced via its neck 2a, into the intracorporeal cavity; and its outer surface is chosen to be biocompatible with the inner wall of the intracorporeal cavity;

a means 3 for transferring the body fluid, said means being mounted at least in part in the interior of the conduit element 2, and extending from a peripheral ring or zone 3a for sampling of the body fluid, protruding radially and to the outside of the neck 2a of said conduit element 2, to an axial collection point 3b for said fluid, situated inside said conduit element 2, toward the base 2b thereof. The ring 3a is supported in the aperture of the neck 2a of the conduit element 2 and forms a passage, for example axial, for communication between the intracorporeal cavity and the inside of the conduit element.

The conduit element 2 can have a composite structure and can comprise a relatively rigid tube 5, for example made of transparent plastic material, with a neck 5a and a base 5b on which is fitted, if appropriate, a biocompatible sleeve 6 surrounding at least the side wall of the tube, consisting for example of an outer tube 6a made of compounds of natural origin, such as cellulose or cotton, and a rigid inner matrix 6b made of polymer as a support for said second tube, whose anterior edge (in the direction of introduction of the device) is rounded, and whose posterior edge is straight.

The transfer means 3 is mounted at least in part in the conduit element 2; preferably however, and as is illustrated in FIG. 1, the transfer means 3 is mounted on a support means 4 which is removable or fixed in relation to the conduit element 2. More specifically, the support means 4 has a funnel shape and is mounted on the rigid tube 5 by means of a screw pitch 5e and a shoulder 5d which are provided on the tube 5 at the level of its neck 5a.

The transfer means 3 comprises a bundle of filiform elements 3c, preferably hollow and hydrophilic filaments, which are gathered together at one end at the axial collection point 3b, and are spread out at the other end about the peripheral sampling ring 3a, each filiform element 3c ensuring the transfer of the body fluid, which is to be recovered, from the outside of the device toward a reaction means, which will be described hereinafter, for example by absorption or capillarity.

These filiform elements 3c can be replaced by other elements ensuring a capillary migration, or a migration by surface tension, of the fluid collected. However, the particular advantage of using the filaments or fibers is that they bend and rub against the intracorporeal wall of the cavity via the peripheral ring 3a of the transfer means 3 upon insertion of the device into said cavity, thereby recovering more fluid than is possible by simple gravitational flow.

Hydrophilic fibers are preferably chosen because these convey the cervical mucus, which consists for the most part of water, more rapidly toward the reaction means, and in particular fibers made of hydrophilic natural or synthetic biocompatible polymers, such as polyesters, polyacrylonitriles, polycarbonates, polyethylenes and polypropylenes, silicones, alginates, polyurethane foams, or else cellulose or its esters. These fibers can be impregnated with a fluid liquefying, or aiding the transport of, the body fluid.

A removal line 15 in the form of a string or cord is fixed to the conduit element 2, on the side of its base 2b, by way of a groove 5c provided in the tube 5.

A reaction means or system 9 is arranged inside the conduit element 2, at its base 2b, facing or in relation with the axial collection point 3b of the transfer means 3, in order to receive some of the body fluid which has been collected. This reaction means incorporates at least one reagent, and if appropriate a liquefying agent for the cervical mucus. This reaction means or system is deposited for example either directly or on an absorbent layer 12. It is capable of reacting with at least one component of the body fluid which has been collected, in order to give at least one color reaction product, which can be directly identified by the user, revealing the presence of said component in the body fluid. As has already been mentioned, the color reagent on its absorbent layer 12 is arranged against the base 2b, facing the axial collection point 3b of the transfer means 3, and more precisely against the transparent base wall 10 of the tube 5. The layer 12 impregnated with the reagent 9 is covered by a web 11 which is semipermeable, in the sense that it is permeable with respect to the body fluid in the direction of transfer, while it holds back this same fluid in the other direction. This web can also be impregnated with a liquefying agent for the cervical mucus, promoting the passage of the compounds which are to be detected and being, for example, a surface-active agent.

In a general manner, although not represented in FIG. 1, the shape and the dimensions of the conduit element 2 are adapted to those of the vaginal cavity.

Figure 2:
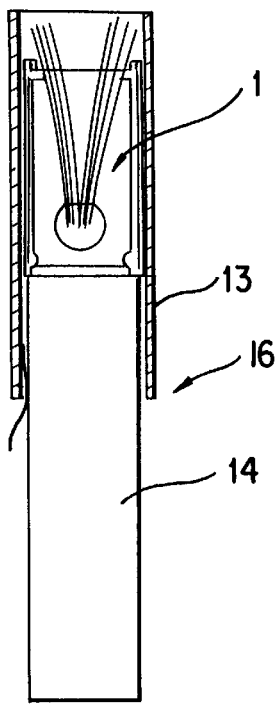
FIG. 2 represents an assembly ready for use, comprising a device according to FIG. 1 together with an applicator system.

In accordance with FIG. 2, the device described above can form part of a ready-to-use assembly comprising this same device 1 and an applicator system 16. The latter comprises a guide tube 13, inside which the recovery device 1 is inserted. A pusher 14 is housed inside the guide tube, abutting against the analysis device. Such an assembly can be introduced directly into the intracorporeal cavity, for example the vaginal cavity, and by pushing the pusher 14 the analysis device 1 is released from the applicator system, in order to position said device in this same cavity.

Figure 3:
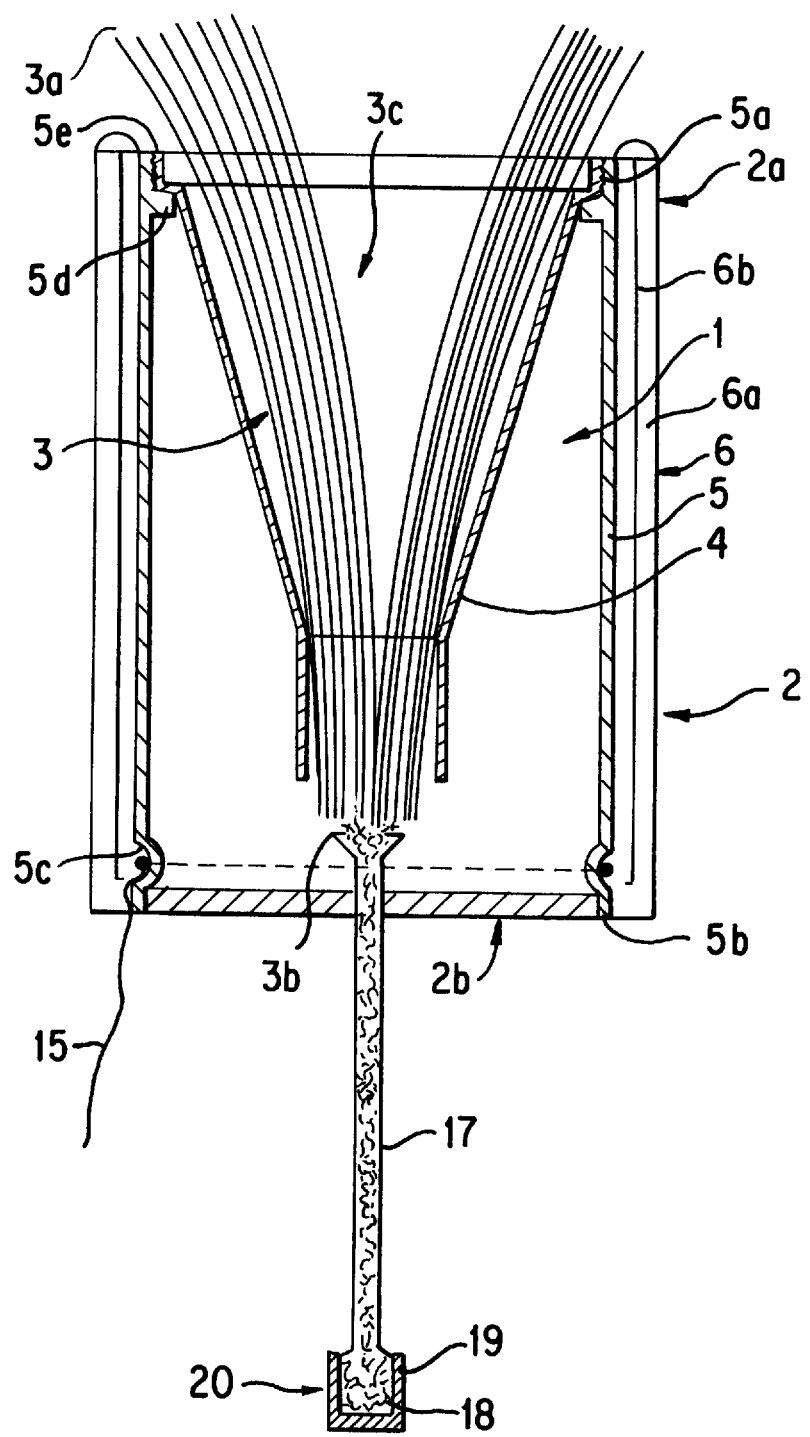
FIG. 3 represents a cross section of a disposable device according to another variant of the invention.

FIG. 3 shows a variant of the invention, in accordance with which the device is essentially the same as that described above, but with the difference that the base 2b is equipped with an aperture, and a stem 17 for transfer of the body fluid passes through said aperture and emerges from the conduit element 2 toward a distal element 20 for recovery of said fluid, this element 20 being equipped with a reaction means 19.

This reaction means can be the same as, or different from, that which has already been described, depending on whether the aim is to reveal the presence of one or more biological components or biological states.

The stem 17, which can be a sheath of rigid or flexible polyethylene or similar, also comprises filiform elements 18 on the inside, these either being the same as for the device illustrated in FIG. 1, or else different, the proviso being that they guarantee the transfer of the body fluid from the axial collection point 3b toward the reaction means 19 of the distal element 20.

The analysis devices described above can therefore be used not only for the detection of a component in a body fluid, but also for detecting any chemical, biochemical or biological state of this same body fluid, for diagnostic, prophylactic or therapeutic purposes. This means that this analysis device can incorporate very different reagents or reaction systems, of a purely chemical type, for example enzymatic, or biological, for example an antigen or an antibody, or else immunoenzymatic.

Consequently, an analysis device according to the invention can have very broad applications, among which there may be mentioned:

the detection of a hormone, and in particular of a hormonal peak;

the sampling and the histological and/or cytochemical analysis of a body fluid, in particular for detecting pathological conditions, or for demonstrating certain physiological phases of a natural cycle, for example of a hormonal cycle.

The following reagents will be mentioned in particular, by way of example, for the detection of a glycoprotein or of a mucopolysaccharide, and consequently of the fertile period in women: safranin, toluidine blue O, Alcian blue, trypan blue, a tolonium salt, PAS (periodic acid-Schiff), alkaline phosphatase or a mixture of these, if appropriate combined with an agent promoting the color reaction, such as polyvinylpyrrolidone.

I claim:

1. A disposable device for analysis of a body fluid present in an elongate intracorporeal cavity, comprising:

a conduit element having respectively, at its two ends, a neck and a base, the conduit element being sufficiently stiff and rigid along its length for it to be pushed via the base to enter the intracorporeal cavity;

a transfer means for transferring the body fluid, said transfer means being mounted at least in part in the interior of the conduit element, wherein the transfer means extends between a sampling zone outside the neck of the conduit element for sampling of the body fluid and an axial collection point for said fluid, wherein the axial collection point is situated inside said conduit element, toward its base;

wherein the sampling zone of the transfer means comprises a peripheral ring that is supported in the aperture of the neck of the conduit element and protrudes radially outside of said neck, wherein the transfer means forms a passage for communication between the intracorporeal cavity and the interior of said conduit element, and wherein a reaction means is mounted on the conduit element, in a manner visible to the user, and in relation with the axial collection point, in order to receive at least some of the body fluid which has been collected, and wherein the reaction means comprises at least one reagent capable of reacting to give at least one reaction product that reveals one of the presence of a biological state, biochemical state, and a component in said body fluid.

2. The device as claimed in claim 1, wherein the conduit element is adapted in shape to be fitted and held directly by simple constriction, in the intracorporeal cavity, and wherein the outer surface of the conduit element is biocompatible with the inner wall of the intracorporeal cavity.

3. The device as claimed in claim 1, wherein the transfer means comprises a bundle of filiform elements which are gathered together at one end at the axial collection point and are spread out at the other end about the peripheral ring, each filiform element being capable of conveying the body fluid from an outer end to an inner end.

4. The device as claimed in claim 3, wherein the filiform elements are hollow filaments.

5. The device as claimed in claim 3, wherein the filiform elements comprise fibers of at least one biocompatible polymer selected from the group consisting of hydrophilic natural polymers, synthetic polymers, silicones, polyurethane foams, cellulose and cellulose esters.

6. The device as claimed in claim 1, wherein the reaction means is arranged inside a closed base of the conduit element, and wherein the reaction means faces the axial collection point of the transfer means.

7. The device as claimed in claim 6, wherein the reaction product is colored, the base of the conduit element is transparent, and the reagent is arranged in a relatively thin layer against the base, facing the axial collection point of the transfer means.

8. The device as claimed in claim 7, wherein the layer of reagent is covered by a semi-permeable web that is permeable to the body fluid in the direction of transfer and substantially impermeable to the body fluid in a direction opposing the direction of transfer.

9. The device as claimed in claim 1, wherein the base comprises an aperture, and wherein a stem for transfer of the body fluid, from the axial collection point to a distal element for recovery of said fluid, passes through the base via the aperture and emerges from the conduit element.

10. The device as claimed in claim 9, wherein the reaction means is associated with the distal element for recovery of the body fluid.

11. The device as claimed in claim 1, wherein the conduit element further comprises a relatively rigid tube with a neck and a base.

12. The device as claimed in claim 1, wherein the transfer means is mounted on a support means attached to the conduit element.

13. The device of claim 12, wherein the support means is removably attached to the conduit element.

14. The device of claim 12, wherein the support means is permanently attached to the conduit element.

15. The device of claim 3, wherein the filiform element conveys the body fluid by at least one of absorption and capillarity.

16. The device of claim 5, wherein the synthetic polymer comprises a polyester.

17. The device of claim 5, wherein the filiform elements are impregnated with an agent for liquefying the body fluid.

18. The device of claim 8, wherein at least one of the web and the reagent layer is impregnated with a liquefying agent that promotes the passage of the body fluid.

19. The device of claim 11, further comprising a biocompatible sleeve surrounding at least a sidewall of said tube.

20. An assembly ready for use, comprising a device as claimed in claim 1, and an applicator system for positioning the device in the elongate intracorporeal cavity.

* * * * *